(12) United States Patent
Chang et al.

(10) Patent No.: US 10,420,536 B2
(45) Date of Patent: Sep. 24, 2019

(54) SOFTWARE-BASED ULTRASOUND IMAGING SYSTEM

(71) Applicant: ALPINION MEDICAL SYSTEMS CO., LTD., Hwaseong-si, Gyeonggi-do (KR)

(72) Inventors: Sun-yeob Chang, Seoul (KR); Ja-woon Koo, Seoul (KR); Seung-pum Kang, Yangju-si (KR); Keonho Son, Seongnam-si (KR)

(73) Assignee: ALPINION MEDICAL SYSTEMS CO., LTD. (KR)

( * ) Notice: Subject to any disclaimer, the term of this patent is extended or adjusted under 35 U.S.C. 154(b) by 120 days.

(21) Appl. No.: 15/125,805

(22) PCT Filed: Mar. 14, 2014

(86) PCT No.: PCT/KR2014/002198
§ 371 (c)(1),
(2) Date: Sep. 13, 2016

(87) PCT Pub. No.: WO2015/137543
PCT Pub. Date: Sep. 17, 2015

(65) Prior Publication Data
US 2017/0000464 A1 Jan. 5, 2017

(51) Int. Cl.
*A61B 8/00* (2006.01)
*G01S 7/52* (2006.01)
(Continued)

(52) U.S. Cl.
CPC ........... *A61B 8/565* (2013.01); *A61B 8/4483* (2013.01); *A61B 8/5207* (2013.01);
(Continued)

(58) Field of Classification Search
None
See application file for complete search history.

(56) References Cited

U.S. PATENT DOCUMENTS 6,526,163 B1 * 2/2003 Halmann ............ G01S 7/52044
382/128
6,532,509 B1 * 3/2003 Wolrich ................ G06F 9/3851
710/240
(Continued)

FOREIGN PATENT DOCUMENTS

JP 2012011193 A 1/2012
JP 2012020127 A 2/2012
(Continued)

OTHER PUBLICATIONS

Chinese Office Action for Application No. 2014-80077182.0 dated Jul. 27, 2018 with English translation (16 pages).
(Continued)

*Primary Examiner* — Elias Mamo
(74) *Attorney, Agent, or Firm* — Harness, Dickey & Pierce, P.L.C.

(57) ABSTRACT

A software-based ultrasound imaging system is disclosed. According to some embodiments of the present disclosure, a method and an architecture for efficiently transmitting, processing, and storing channel data in the software-based ultrasound imaging system are provided.

35 Claims, 12 Drawing Sheets

(51) Int. Cl.
*A61B 8/08* (2006.01)
*G06F 13/16* (2006.01)
*G06F 13/28* (2006.01)

(52) U.S. Cl.
CPC ...... *G01S 7/52082* (2013.01); *G06F 13/1673* (2013.01); *G06F 13/28* (2013.01); *A61B 8/461* (2013.01)

(56) References Cited

U.S. PATENT DOCUMENTS

| | | | |
|---|---|---|---|
| 8,220,334 B2* | 7/2012 | Klessel | G01S 7/52028 |
| | | | 310/322 |
| 8,287,456 B2 | 10/2012 | Daigle | |
| 8,395,631 B1 | 3/2013 | Wilt | |
| 8,619,000 B2* | 12/2013 | Shinkawa | H01Q 7/00 |
| | | | 343/700 MS |
| 2004/0015079 A1 | 1/2004 | Berger et al. | |
| 2004/0083311 A1* | 4/2004 | Zhuge | G06F 15/7867 |
| | | | 710/1 |
| 2009/0112095 A1 | 4/2009 | Daigle | |
| 2011/0074792 A1* | 3/2011 | Li | A61B 8/4411 |
| | | | 345/519 |
| 2012/0004545 A1 | 1/2012 | Ziv-Ari et al. | |
| 2012/0010508 A1 | 1/2012 | Sokulin et al. | |
| 2012/0215110 A1* | 8/2012 | Wilkening | A61B 8/488 |
| | | | 600/453 |
| 2013/0190622 A1 | 7/2013 | Daigle | |
| 2015/0011880 A1 | 1/2015 | Kim et al. | |
| 2015/0113252 A1* | 4/2015 | Moy | G06F 9/3851 |
| | | | 712/215 |
| 2015/0216511 A1* | 8/2015 | Tur | A61B 8/565 |
| | | | 600/443 |
| 2015/0374342 A1 | 12/2015 | Son et al. | |
| 2016/0007960 A1 | 1/2016 | Son et al. | |
| 2016/0074013 A1 | 3/2016 | Chae et al. | |

FOREIGN PATENT DOCUMENTS

| | | |
|---|---|---|
| JP | 2012187418 A | 10/2012 |
| JP | 2013-0154169 A | 8/2013 |
| KR | 1020120125076 A | 11/2012 |
| TW | 2011-11823 A | 4/2011 |

OTHER PUBLICATIONS

International Search Report (in English and Korean) for PCT/KR2014/002198, dated Dec. 8, 2014; ISA/KR.

* cited by examiner

SOFTWARE-BASED ULTRASOUND IMAGING SYSTEM

CROSS REFERENCE TO RELATED APPLICATIONS

This application is a U.S. National Phase application under 35 U.S.C. 371 of International Application No. PCT/KR2014/002198 filed on Mar. 14, 2014 and published in Korean as WO 2015/137543 A1 on Sep. 17, 2015. The entire disclosure of the above application is incorporated herein by reference.

TECHNICAL FIELD

The relates to an ultrasound imaging system, and more particularly, the present disclosure relates to a software-based ultrasound imaging system with improvements in data transmission, memory access method, and the like.

BACKGROUND

The statements in this section merely provide background information related to the present disclosure and do not necessarily constitute prior art.

An ultrasound imaging system is widely used in a medical field to acquire internal information of a subject by using a reflected signal obtained by transmitting an ultrasound to the subject and receiving a signal reflected from the inside of the subject. The ultrasound imaging system is a sophisticated electronic system that requires acquisition and realtime process of multichannel ultrasound signals. In particular, a digital beamforming constitutes the most operation-intensive functional block in the ultrasound imaging system, which is designed based on a hard-wired structure, e.g., ASICs (Application Specific Integrated Circuits) and FPGA (Field Programmable Gate Array). In recent years, with a rapid development of software processing, particularly a parallel core processor, including a general purpose graphics processing unit (GPGPU) and a Many Integrated Core (MIC) processor, has enabled making attempts to implement such hardware functions with software.

Such a software-based ultrasound imaging system processes ultrasound data acquired in realtime on a host apparatus that is run on an operating system operating in a non-realtime basis, and in this sense, the issue is to design a scheme for transmitting the ultrasound data and processing the same in guaranteed real-time.

DISCLOSURE

Technical Problem

The present disclosure has been achieved in view of the above aspects, and it is an object of the present disclosure to provide a software-based ultrasound imaging system with improved data transmission and memory access method and a method of generating an ultrasound image by using the ultrasound imaging system.

SUMMARY

According to some embodiments of the present disclosure, when transmitting channel data to a host PC, a front-end unit directly transmits the channel data to a system memory of the host PC by way of a bus mastering of a data bus, without an aid of an additional memory. In addition, the ultrasound imaging system causes the channel data to be stored in the system memory in a state in which the channel data are aligned in the order of transducer elements by controlling a destination address of data for each channel.

In some embodiments of the present disclosure, the host PC page-locks a first predetermined area of the system memory, and the front-end unit directly transmits the channel data to the page-locked area. Address information of the page-locked area is linked to the front-end unit and the parallel core processor, to allow the front-end unit and the GPU to access the page-locked area simultaneously. Further, the host PC page-locks a second predetermined area of the system memory, and stores an output of a predetermined step in an image generation process based on the channel data in the page-locked area. The host PC is configured to use the page-locked areas of the system memory as a cine memory.

In some embodiments of the present disclosure, in performing at least one sub-process among processes for forming an ultrasound image, the host PC uses a multi-thread processing method with the parallel core processor. In addition, in order to increase the processing speed of the parallel core processor, when copying data between the system memory and a local memory of the parallel core processor, the host PC copies the data based on an asynchronous transmission by dividing the data while using a streaming technique in which data copy and data processing are performed in an overlapped manner.

According to some embodiments of the present disclosure, an ultrasound diagnostic apparatus includes a front-end unit configured to be electrically connected to a transducer and a host PC configured to receive channel data from the front-end unit via a data bus and to process the channel data. The host PC includes a system memory, at least one parallel core processor, and a central processing unit (CPU) configured to page-lock a predetermined area (hereinafter, "first area") in the system memory. The front-end unit is configured to transmit the channel data to the first area in a direct memory access (DMA) scheme, and the parallel core processor is configured to access the first area in the DMA scheme and to perform at least a part of processes for generating an ultrasound image, in a multi-thread processing scheme.

According to some embodiments of the present disclosure, a front-end unit configured to be electrically connected to a transducer includes an analog-to-digital (A/D) converter configured to convert an RF signal transmitted from the transducer in real time into a digital signal, a buffer memory configured to buffer an output of the A/D converter for each channel, and a processing circuit configured to generate a data packet as large as a maximum payload size of the data bus based on channel-specific data to be buffered in the buffer memory in a round-robin scheme and to transmit the channel-specific data to a page-locked area in the system memory of the host PC regardless of a data request from the host PC.

According to some embodiments of the present disclosure, a host PC for an ultrasound diagnostic apparatus includes a front-end unit configured to be electrically connected to a transducer and a host PC configured to receive channel data from the front-end unit via a data bus and to process the channel data. The host PC includes a system memory, at least one parallel core processor, and a central processing unit (CPU) configured to page-lock a predetermined area or "first area" in the system memory. The front-end unit is configured to perform a transmission of the channel data to the first area in a direct memory access (DMA) scheme. The parallel core processor is configured to access the first area in the DMA scheme and to perform at least a part of processes for generating an ultrasound image, in a multi-thread processing scheme.

Some embodiments of the present disclosure provide a method for generating an ultrasound image by an ultrasound diagnostic apparatus that includes a front-end unit configured to be electrically connected to a transducer and a host PC configured to receive channel data from the front-end unit via a data bus and to process the channel data. The method includes page-locking, by the host PC, a predetermined area or "first area" in a system memory, acquiring, by the front-end unit, the channel data by using the transducer, transmitting, by the front-end unit, the channel data to the first area, and performing processes for generating an ultrasound image based on the channel data by using a central processing unit (CPU) and a parallel core processor included in the host PC. The front-end unit and the parallel core processor are configured to simultaneously access the first area in a direct memory access (DMA) scheme.

According to some embodiments of the present disclosure, a non-transitory computer-readable storage medium stores computer-executable instructions for causing, when executed by a computer that includes a system memory, a central processing unit (CPU) and a parallel core processor, the computer to execute page-locking a predetermined area or "first area" in the system memory, performing processes for generating an ultrasound image based on the channel data that is transmitted to the first area in a direct memory access (DMA) scheme from a front-end unit connected via a data bus, and allowing the parallel core processor to access the first area in the DMA scheme and to perform at least a part of the processes for generating the ultrasound image in a multi-thread processing scheme.

Advantageous Effects

Some embodiments of the present disclosure, as described above, provide a method and an architecture for efficiently transmitting, processing, and storing channel data in the software-based ultrasound imaging system.

Further, according to some embodiments of the present disclosure, the front-end unit directly transmits the channel data to the system memory via bus mastering without an intervention of the CPU of the host PC, and hence a time delay in the data transmission is minimized.

Moreover, according to some embodiments of the present disclosure, at the same time as the transmission of the channel data from the front-end unit to the system memory, per-channel sample values are stored by being aligned in the order of transducer elements, which increases the coalescing of the data and improves the efficiency of the memory access when the host PC performs operations on the channel data, e.g., a beamforming operation.

Further, according to some embodiments of the present disclosure, when copying data between a local memory of the GPU and the system memory, the data are divided and transmitted by an asynchronous transmission with the data transmission and data processing performed simultaneously in an overlapped manner, and hence the latency in the data copying can be fully hidden behind the operation of the GPU.

Moreover, according to some embodiments of the present disclosure, a page-locked space in the system memory can be used as a cine memory, and thereby the GPU can be utilized in a more efficient manner in the process of loading a stored data file to the page-locked space in the system memory and reconstructing an ultrasound image.

DETAILED DESCRIPTION

Figure 1:
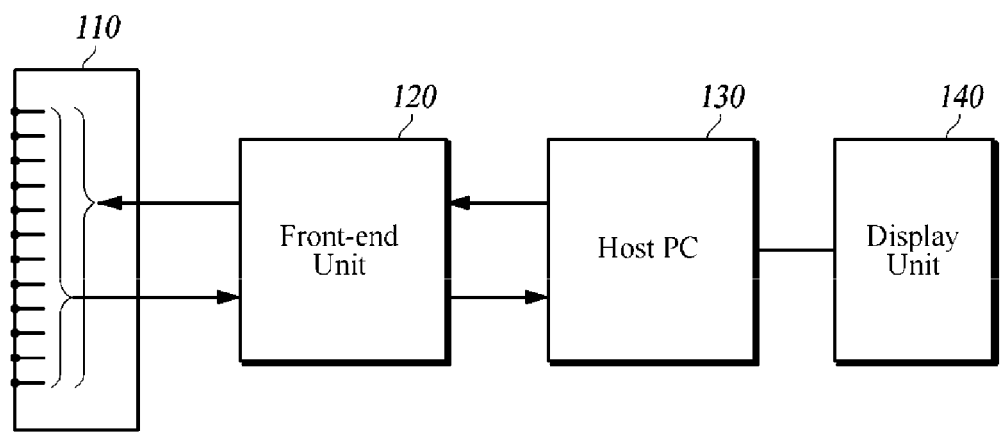
FIG. 1 is a block diagram of an ultrasound imaging system according to some embodiments of the present disclosure.

Hereinafter, at least one embodiment of the present disclosure will be described in detail with reference to the accompanying drawings. In the following description, like reference numerals designate like elements although the elements are shown in different drawings. Further, in the following description of the at least one embodiment, a detailed description of known functions and configurations incorporated herein will be omitted for the purpose of clarity and for brevity.

Additionally, in describing the components of the present disclosure, various terms such as first, second, A, B, (a), (b), etc., are used solely for the purpose of differentiating one component from another, and one of ordinary skill would understand the terms are the other but not to imply or suggest the substances, order or sequence of the components. It will be further understood that the terms "comprises" and/or "includes", when used in this specification, do not preclude presence or addition of one or more other elements, unless otherwise stated, but mean to further include one or more other elements. In the following description, suffixes such as 'unit' or 'module' used for referring to elements mean a unit to process at least one function or operation, which can be implemented by hardware, software, or a combination thereof.

FIG. 1 is a block diagram of an ultrasound imaging system according to some embodiments of the present disclosure.

As shown in FIG. 1, the ultrasound imaging system is electrically connected to an ultrasound transducer 110 and a display unit 140. The ultrasound imaging system includes a front-end unit 120 and a host PC 130.

The front-end unit 120 generates an electrical drive signal to be applied to the ultrasound transducer based on a control signal transmitted from the host PC 130. The ultrasound transducer 110 converts the electrical drive signal supplied by the front-end unit 120 into an ultrasound signal and transmits the ultrasound signal to a subject, and receives a reflected signal of the transmitted ultrasound signal from the subject and converts the reflected signal into an electrical signal (i.e., RF signal). The term 'RF' is typically used in the pertinent technical field, which means a frequency of the ultrasound (typically 0.5 MHz to 100 MHz); however, this does not limit the scope of the present disclosure.

Although several transducer elements are demonstrated in the example shown in FIG. 1, in general, the ultrasound transducer includes a few hundreds of (e.g., 128 or 256) transducer elements. As well known in the pertinent art, the RF signal can be acquired for each scanline or can be acquired in units of frame by using a plane wave or a divergent wave. The RF signal can be used to generate a two-dimensional image or a three-dimensional image of a region-of-interest in the subject.

The front-end unit 120 converts the RF signal that is an analog signal into a digital signal, and transmits the digital signal to the system memory of the host PC 130 in the DMA scheme via a bus mastering for the data bus (e.g., PCI Express bus). Before or after its analog-to-digital conversion, the RF signal may undergo different processing including a low-pass filtering, an anti-aliasing filtering, a pulse compression, a band-pass filtering, an IQ demodulation and a decimation; however, even in such a case, ultrasound data after a minimum processing are stored in the system memory.

The front-end unit 120 can be implemented in various ways in a probe or the host PC 130, and alternatively, separately from the probe and the host PC 130 as an independent unit. For example, the front-end unit 120 can be implemented in the probe in a board-to-board (BTB) connection, or formed to be plugged in to a main board of the host PC 130. Alternatively, the front-end unit 120 can be located outside the host PC 130 and can be connected to the host PC 130 via a data bus.

The host PC 130 controls the front-end unit 120 to acquire the ultrasound data, and drives software that is used to generate the ultrasound image, by processing the acquired ultrasound data.

The ultrasound imaging system having the above-mentioned configuration simplifies the front-end unit that is constituted with dedicated hardware (e.g., FPGA), and it is readily capable of applying a new mode other than the well-known modes such as a B mode, an M mode, and the like and a new beamforming mode by way of a modification of the software. That is, a part of the software can be easily modified to meet various requirements from users throughout the development of the ultrasound imaging system. Consequently, the present disclosure offers the advantages of developing the ultrasound imaging system easily and expanding the functions of the ultrasound imaging system easily.

Figure 2:
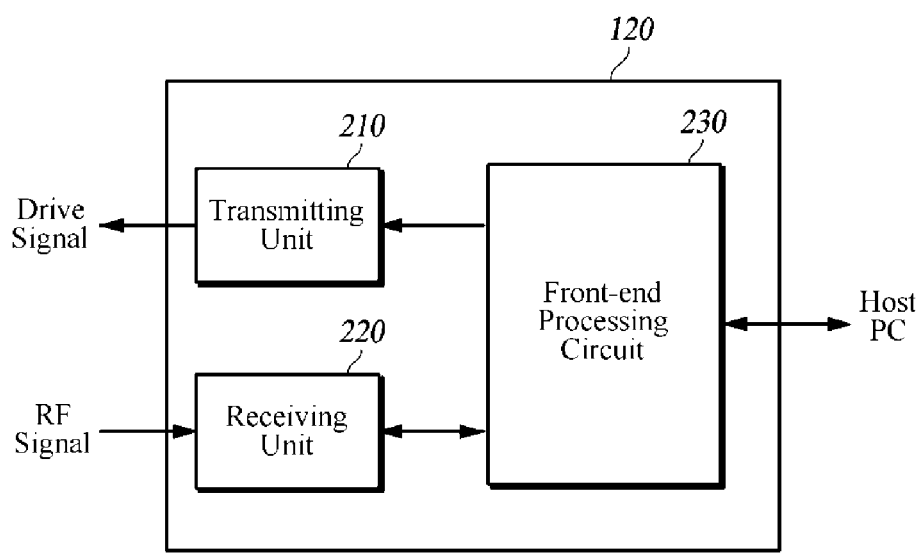
FIG. 2 is a block diagram of a front-end unit according to some embodiments of the present disclosure.

FIG. 2 is a block diagram of the front-end unit according to some embodiments of the present disclosure.

As shown in FIG. 2, the front-end unit 120 includes a transmitting unit 210, a receiving unit 220 and a front-end processing circuit 230. The front-end unit 120 can further include other constituent elements depending on its function, although their configurations will not be elaborated herein not to obscure the gist of the present disclosure in describing the method for transmitting the data to the host PC, which is one of the features of the present disclosure.

The transmitting unit 210 generates the electrical drive signal to be applied to the ultrasound transducer 110 based on the control signal transmitted from the host PC 130 via the front-end processing circuit 230. Although it is instantiated in some embodiments that the transmitting unit 210 is included in the front-end unit 120, the transmitting unit 210 can also be configured separately from the front-end unit 120.

The receiving unit 220 may include a receiving circuit, N analog-to-digital or A/D converters and N buffer memories. The reflected signal (echo) from the subject is converted into the electrical signal (i.e., RF signal) by the ultrasound transducer 110, and the receiving circuit receives the RF signal from the ultrasound transducer 110. The A/D converter converts the RF signal in the form of an analog signal, which is an output of the receiving circuit, into the digital equivalent. The digital signal (i.e., sample value for each channel) that is an output of the A/D converter is temporarily buffered for each of channels in the N buffer memories.

The front-end processing circuit 230 obtains information on the address of a page-locked area of the system memory from the host PC 130 connected via a data bus. Here, the address information may be the physical address of the page-locked area or a virtual address mapped to the physical address, i.e., it may be a logical address. The front-end processing circuit 230 transmits the sample value of each channel, buffered in the buffer memory 223, through a bus mastering for the data bus directly to the system memory of the host PC 130. In other words, the front-end processing circuit 230 utilizes the DMA technique. The data bus can use the appropriate high-speed bus technology that can ensure real-time transmission. For example, a data bus 550 may be implemented by a PCIe (PCI Express) bus. In some embodiments of the present disclosure, the front-end processing circuit 230 may include a DMA controller for performing a DMA transfer of respective channel sample values buffered in the buffer memory through the data bus to the system memory of the host PC 130, and a control unit which controls the DMA controller to perform a DMA transfer in response to a certain magnitude of the sample values buffered in the buffer memory.

In some embodiments, before or after the digital conversion of the RF signal, the front-end unit 120 may carry out pre-processing such as a low-frequency filtering, anti-aliasing filtering, pulse compression, band-pass filtering, IQ demodulation and decimation. Thus, data transferred to the system memory of the host PC 130 can have various formats depending on the pre-processing scheme that is performed by the front-end unit 120. For example, if the front-end processing circuit 230 is configured to perform an IQ demodulation, the system memory may have IQ data demodulated by the baseband transmitted thereto. Hereinafter, the data transmitted to the system memory of the host PC will be referred to as "channel data."

Figure 3:
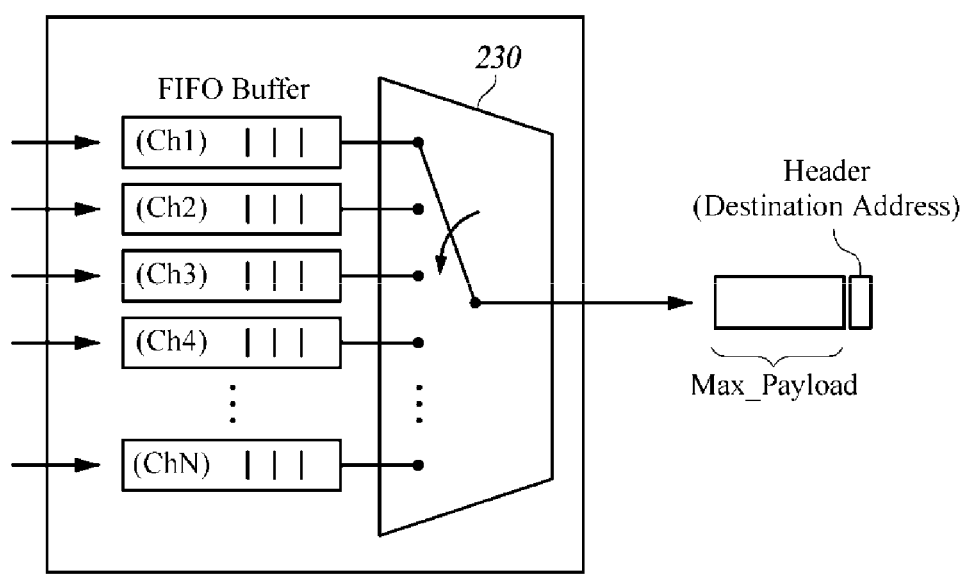
FIG. 3 is a schematic diagram showing a data transmission mode of the front-end unit according to some embodiments of the present disclosure.
Figure 4:
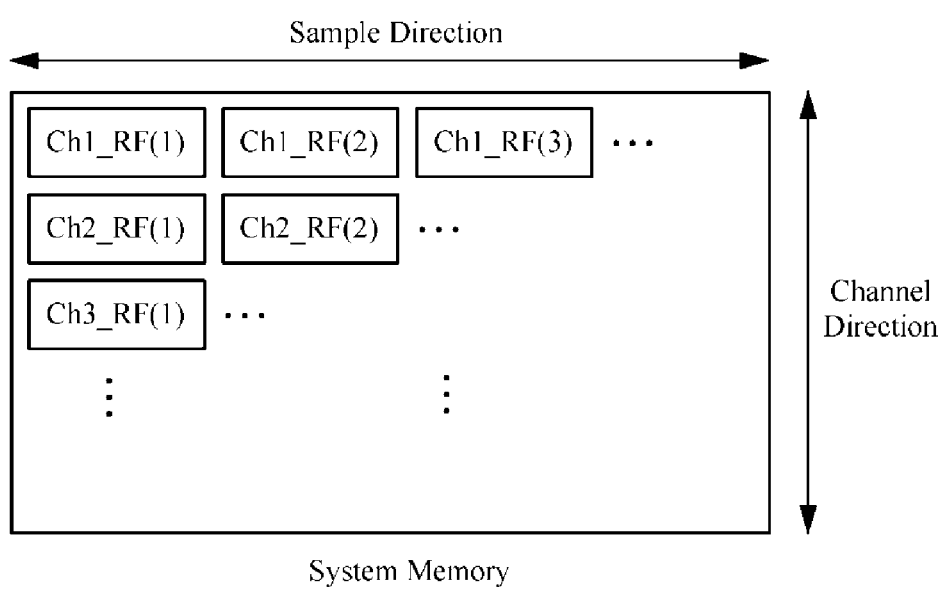
FIG. 4 is a schematic diagram showing an alignment form of channel data stored in a system memory of a host PC according to some embodiments of the present disclosure.

A method of transmitting channel data to a system memory of the host PC 130 by the front-end unit 120 is described in detail below with reference to FIGS. 3 and 4. FIG. 3 is a schematic diagram showing a data transmission mode of the front-end unit according to some embodiments of the present disclosure; and FIG. 4 is a schematic diagram showing an alignment form of channel data stored in the system memory of the host PC according to some embodiments of the present disclosure.

As described above, the respective channel sample values output from the A/D converters are buffered by the first-in first-out (FIFO) method in the respective channel buffer memories of the receiving unit 220. The front-end processing circuit 230 generates, for each of the respective channel buffers, a data packet in a round-robin scheme, and transmits the same to the host PC 130. In other words, data packets are generated sequentially, channel by channel. At this time, the front-end processing circuit 230 generates the data packet on the basis of Max_Payload_Size determined by the data bus protocol, and transmits the generated data packet to respective channel destination addresses in the system memory.

The front-end processing circuit 230 obtains, in advance from the host PC 130, information on the address of the page-locked area on the system memory. Here, the address information may be the physical address of the page-locked area or a virtual address mapped to the physical address, i.e., it may be a logical address. Based on the above address information, the front-end processing circuit 230 assigns a destination address to which sample values included in each data packet will be stored. The destination address assignment is performed so that sample values are stored in continuous address spaces for each channel. In addition, the per-channel destination addresses are assigned so that the storing process is performed in order from the start index of the memory array and that, at the end of indices, the storing returns to the start index and reiterates the storing process therefrom (i.e., in a cyclic manner). Through the control of the destination addresses as described above, simultaneously with their transmission, the channel data sorted by channel (or element) are stored in the system memory. Referring to FIG. 4, in the address space of the system memory, sequentially stored in the vertical direction are per-channel sample values by different channels, and those stored in the lateral direction are sample values in the same channel. In other words, the channel data are stored in the memory address space contiguous for each channel.

The above-mentioned transmission scheme and the channel data storing method in the system memory increase the coalescing of the data, which improves the efficiency of the memory access when the host 130 performs operations on the channel data, e.g., the beamforming operation.

Figure 5:
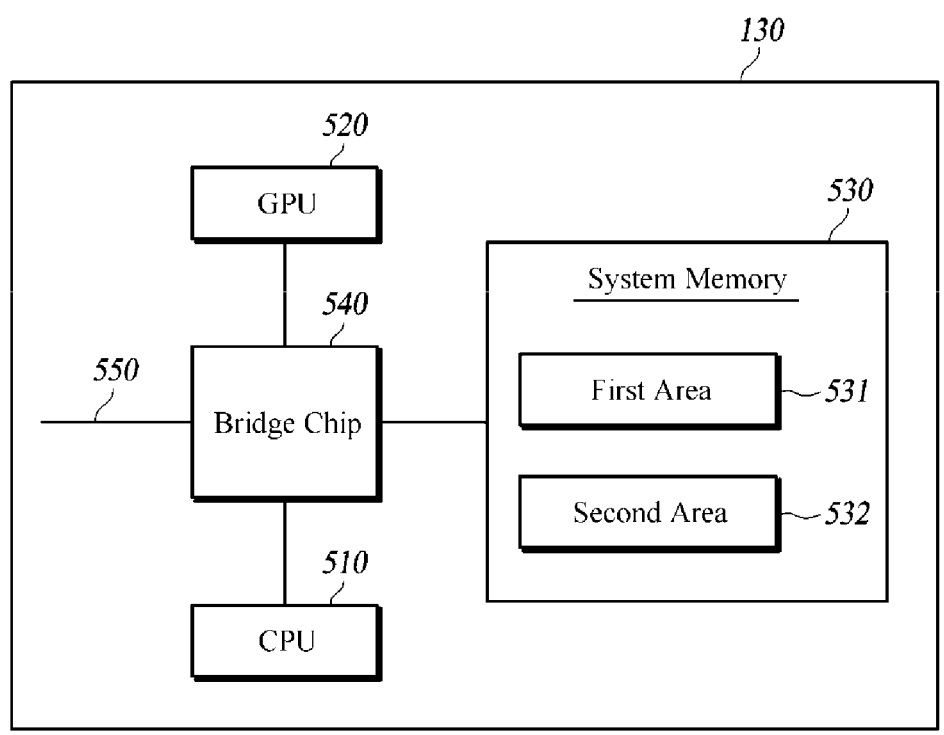
FIG. 5 is a block diagram of the host PC according to some embodiments of the present disclosure.

FIG. 5 is a block diagram of the host PC according to some embodiments of the present disclosure.

As shown in FIG. 5, the host PC 130 according to some embodiments of the present disclosure includes a central processing unit (CPU) 510, a graphics processing unit (GPU) 520, a GPU memory 525, a system memory 530 and a bridge chip 540. Here, the host PC 130, depending on its function, can further include other components, although they will be omitted from the description of configurations not to possibly obscure the described substance of the method for processing the channel data, which is one of the features of the present disclosure. Moreover, the configurations of the host PC 130 in the following are merely exemplary embodiments of the present disclosure, and are not to limit the host PC 130 to the illustrative configurations.

The bridge chip 540 is electrically connected to the front-end unit 120 via the data bus 550. Further, the bridge chip 540 is electrically connected to the CPU 510, the system memory 530 and the GPU 520. The bridge chip 540 may be, for example, a Northbridge chip and it can support the expansion buses for connecting a variety of I/O devices, for example, one or more of a hard disk drive or such a large-capacity storage device, a human-machine interface device, an Ethernet adapter or such a communication adapter, a CD-ROM, DVD, etc. The data bus can use an appropriate high-speed bus technology which transfers channel data in real time. For example, the data bus 550 may be implemented by a PCIe (PCI Express) bus.

The CPU 510 may be a processor widely known to those skilled in the art, such as those manufactured by Intel Corporation or other suppliers. The system memory 530 may be a plurality of DRAM (Dynamic Random Access Memory) devices. The GPU 520 may be disposed on a graphics card, while the CPU 510 and the system memory 530 may be placed on the motherboard of the host PC 130. The graphics card, including the GPU 520 is generally a data PCB (Printed Circuit Board) with the GPU 520 attached. In some other embodiments, the GPU 520 may be included on the motherboard. The illustrated Host PC 130 may also include a plurality of GPUs. These GPUs may each be in a separate graphics card, and in some embodiments, some of the GPUs may also be arranged on the motherboard. In general, a GPU is largely composed of a plurality of streaming multi-processors and off-chip memories, and the streaming multi-processor is constituted by a plurality of stream processors and on-chip memories.

Although it is instantiated in the example shown in FIG. 5 that the bridge chip 540 is electrically connected to the CPU 510, GPU 520 and system memory 530, some embodiments may construct the GPU 520 of the host PC 130 to be electrically connected directly to the CPU 510 and the memory 530, and to the front-end processing circuit 230 via the data bus 550. Further, in some other embodiments, the CPU 510 and the GPU 520 of the host PC 130 may be configured on a single die as an integrated single chip structure adapted to share the system memory 530. Such configuration has advantages in terms of latency, data processing speed among others. In some embodiments, a general purpose GPU (GPGPU) can be used as the GPU 520, while in some other embodiments, a Many Integrated Core (MIC) can be used as a substitute for the GPU 520.

Based on the above-mentioned configuration, the CPU 510 of the host PC 130 controls the front-end unit 120 to obtain the data channel and drives the software for generating an ultrasonic image by using the GPU for processing the channel data in real-time or non-real-time (e.g., in the cine loop). In other words, the CPU 510 controls the operations of the transmitting unit 210 and the receiving unit 220 via the front-end processing circuit 230, and thereby enables the front-end unit 120 to utilize the transducer 110 for obtaining the channel data. In addition, for the purpose of the GPU 520 generating ultrasound image data, the CPU 510 performs an imaging process of the ultrasound scan data by way of multi-thread processing.

1. Pre-Setting

The system memory 530 has a predetermined size of a memory block (a first area 531) page-locked by the CPU 510 to store the channel data received from the front-end unit 120. In other words, the first area 531, in which the channel data is stored, is restricted from paging, and the corresponding memory space is always present only in the system memory. The page-locked memory is also referred to as pinned memory. The system memory 530 has another predetermined size of a memory block (a second area 532) page-locked. The second area 532 is adapted to store further processed data (i.e., beamformed data, I/O data, etc.) that underwent further processes including a beamforming to the channel data stored in the first area 531. It should be understood by those skilled in the art that the system memory 530 may have yet another memory block for storing software executed by the CPU 510.

For the front-end processing circuit 230 to store the channel data in the system memory 530 in the DMA scheme, the CPU 510 provides the front-end processing circuit 230 with the necessary address information of the first area 531. Additionally, for the GPU 520 to obtain the channel data stored in the first area 531 of the system memory 530 in the DMA scheme, the CPU 510 provides the GPU 520 with the necessary address information of the first area 531. The CPU 510 also provides the GPU 520 with the necessary address information of the second area 531 to allow the GPU 520 to store the result of the GPU performing the processing of the channel data. Thereby, the front-end processing circuit 226 and the GPU 520 can simultaneously access to the page-locked first area 531 based on the address information of the first area 531 obtained from the CPU 510 without intervention of the CPU 510. Here, the address information may be the physical address of the page-locked area or a virtual address mapped to the physical address, i.e., it may be a logical address. In ultrasound imaging where the real-time processing is important, a page-locked memory allows for faster memory access than a pageable memory. In other words, the front-end unit 120 and the GPU 520 can access the page-locked memory in the DMA scheme without the intervention of the CPU, which obviates the needs for a copy of data to the buffer of the CPU or such additional data copyies and operations.

Figure 6:
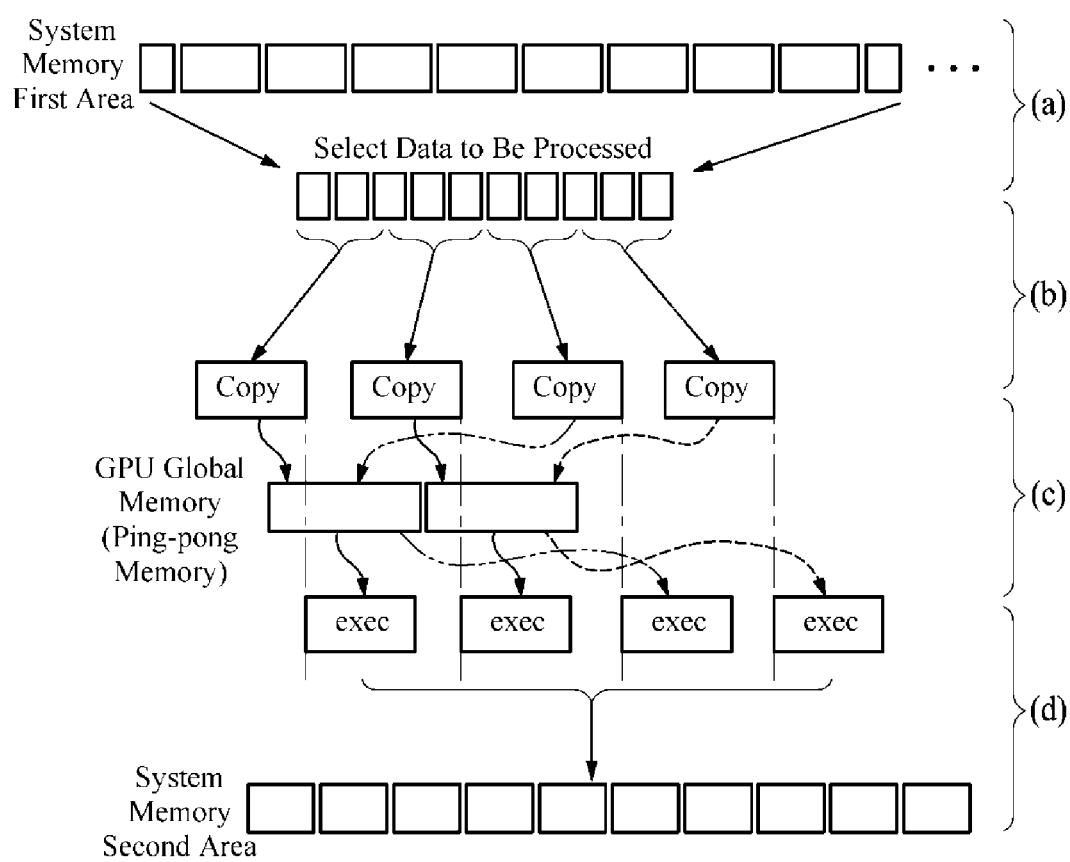
FIG. 6 is a schematic diagram showing a method for copying and processing data by a GPU according to some embodiments of the present disclosure.

A method for copying and processing the ultrasound data stored in the system memory by the CPU is described in detail below with reference to FIG. 6. FIG. 6 is a schematic diagram showing a method for copying and processing data by the GPU according to some embodiments of the present disclosure.

2. Selective Processing of Channel Data

Referring to FIG. 6 at (a), in a real-time operation or non-real-time operation (for example, cine loop operation), the host PC may process only a selective portion of the channel data stored in the first area in the system memory. For example, the ultrasound imaging system may utilize a maximum available pulse repetition frequency (PRF) for obtaining in the first area of the system memory the sufficient channel data that exceeds the real-time processing capability of the host PC. In order to maintain such real-time processing, the host PC processes only a selective portion of the channel data in the first area of the system memory instead of processing all of the obtained channel data therein. Thus, the channel data exceeding the real-time processing capability of the host PC can be effectively utilized in a non-real-time operation. In other words, when the host PC is in real-time processing or in a cine loop operation having (almost) no limitation of frame rate, it can handle the channel data amount more than all the channel data stored in the first area of the system memory or at least the amount possible in the real-time processing.

3. Data Copy and Operation by GPU

The GPU is used to perform the most computationally intensive function of the digital beam forming in the ultrasonic imaging system. Used to perform the image forming process, the GPU is a multi-core parallel processing system, and thus the respective steps of the image forming process can be divided into a plurality of sub-processes and the sub-processes can be assigned to different cores where they are processed at the same time.

Processing data on a system memory using the GPU needs an off-chip memory (global memory) of the GPU to have a copy of the same data. Once the data is copied from the system memory to the global memory of the GPU, the multi-processors in the GPU access data in the global memory for processing thereof. Here, the copying of the data from the system memory to the global memory of the GPU has a high latency due to the bandwidth limitation of the data bus. For example, a PCI-E 2.0×16 bus has a maximum bandwidth limited to 8 GB/s. Transmitting the processed result in the GPU to the system memory also has the issue of similarly high latency.

In consideration of this, some embodiments of the present disclosure do not copy all data (e.g., data constituting a scan line or frame) from the system memory to the GPU local memories (global memory) before starting the computation thereof, but rather divide the entire data into a plurality of blocks (see FIG. 6 at (b)) and perform an overlapped copy and computation (execution) of the divided blocks. In other words, as illustrated in FIG. 6 at (c), at the same time of starting the computation based on the first received data block, the GPU starts to copy the second data block. A typical memory copying requires less time than the GPU execution, which thus can render the GPU execution completely hide the time required for the data copying between the system memory and the graphics card memory.

When applying such concurrent copy and execution method, the global memory of the GPU operate as the so-called "ping-pong memory." In other words, the global memory of the GPU can be operated as a plurality of buffers. In FIG. 6 at (c), a concurrent copy and execution method is illustrated wherein the GPU global memory operates as two buffers. During copying the next data into one buffer, a GPU calculation is performed on the data in another buffer. Through such concurrent copy and execution method can help to shorten the overhead time required for copying data between memories. Further, with a minimal ping-pong memory size secured, it is possible to divide handling a large size of the frame data can be divided and processed, which allows a limited capacity of the GPU memory efficiently. The concurrent copy and execution method also applies to when transmitting the result computed by the GPU to the system memory (see FIG. 6 at (d)).

On the other hand, in order to apply the concurrent copy and execution method, complete data (e.g., data constituting a scanline or frame) are divided and processed (copied and computed) as a plurality of blocks of (see FIG. 6 at (b)), where the division of data needs to be performed dependent on the method for obtaining the channel data stored in the first area of the system memory. For example, in case of transmitting a focused ultrasound to acquire the channel data for each scanline, the block to be divided and processed is better composed of a set of scanlines in one frame. At this time, the size of each block is determined by various factors including a scan depth, the number of scanlines, ensembles, a frame rate and whether the operation is in real-time or non-real-time. In case of obtaining the channel data by using the plane wave, the block to be divided and processed is preferably composed of a set of one or more frames. At that time, the size of each block is determined by various factors including the scan depth, number of scanlines, ensembles, frame rate, number of frames to be synthesized and whether the operation is in real-time or non-real-time. On the other hand, if the order of the data between the copy and the computation by the GPU does not match those of the scanlines and the ensembles, they may be rearranged at the time of outputting the computation result to the system memory.

Of the GPU memories, the memory access speed decreases the most in the on-chip registers, the more in the on-chip shared memory and the least in the off-chip global memory. Accordingly, it is desirable to limit use of the slowest global memory to storing the output data and input data in the beamforming process. In addition, the faster shared memory is desirably used in storing an interim output in the beamforming process, the fastest registers are better used to hold temporary results in sub-steps of the beamforming process. This way of memory allocation is applicable to other sub-steps of the image formation process than the beamforming.

4. Realtime Operation

Figure 7:
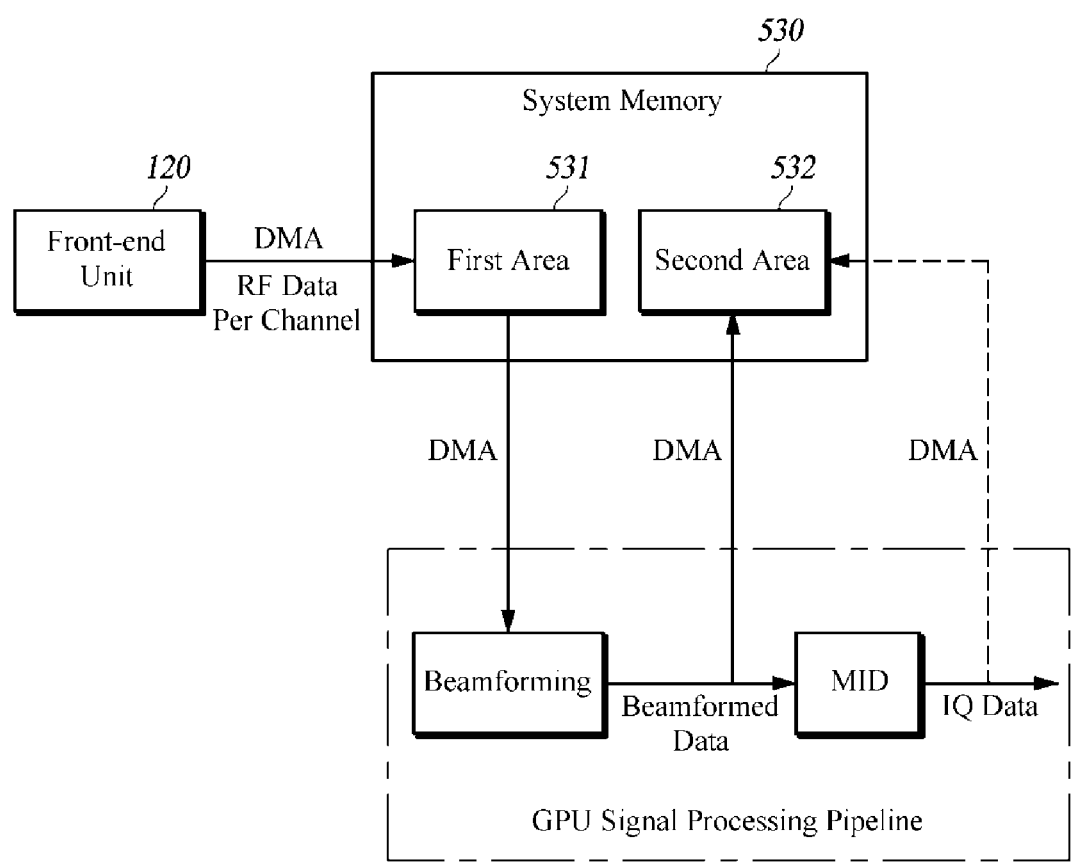
FIG. 7 is a schematic diagram showing a method for processing ultrasound data by the host PC when operating in realtime according to some embodiments of the present disclosure.
Figure 8:
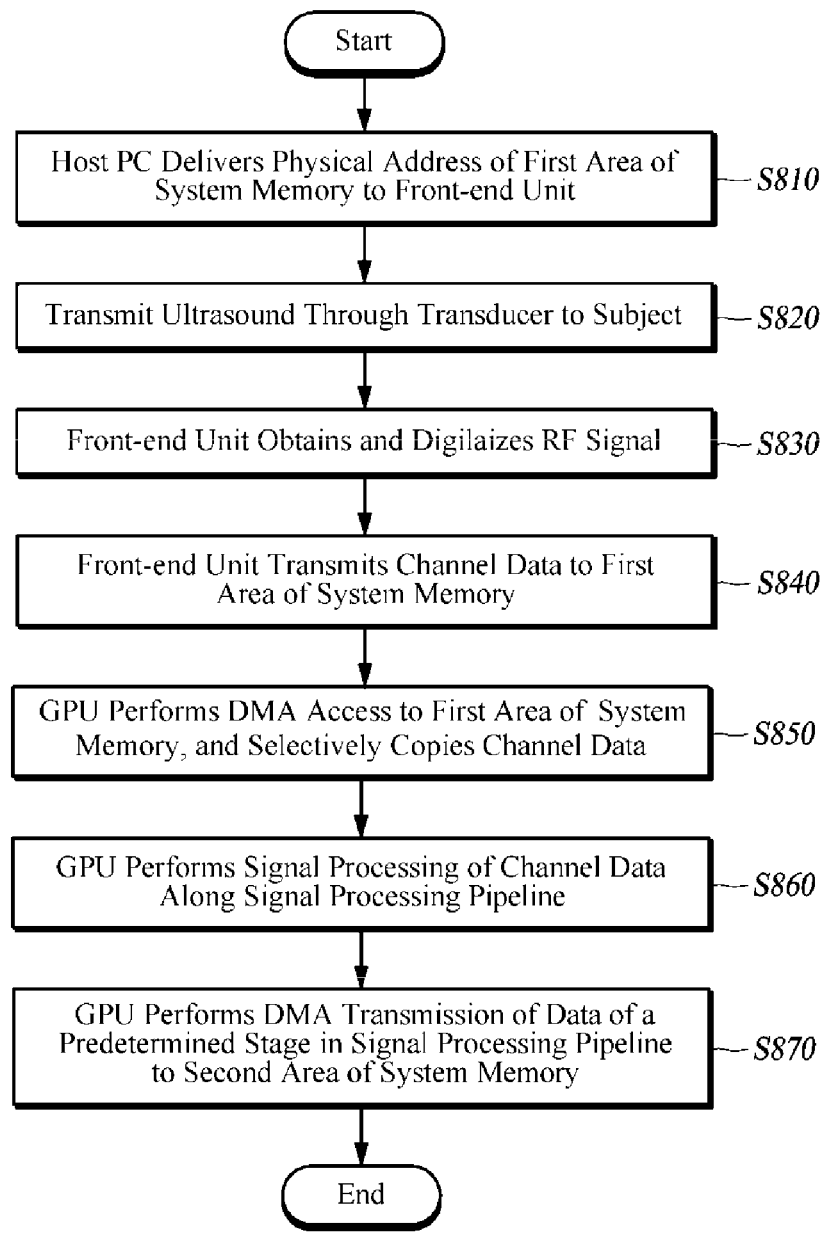
FIG. 8 is a flowchart showing a realtime operation of the ultrasound imaging system according to some embodiments of the present disclosure.

A realtime operation of the ultrasound imaging system is described in detail below with reference to FIGS. 7 and 8. FIG. 7 is a schematic diagram showing a method for processing ultrasound data by the host PC when operating in realtime according to some embodiments of the present disclosure; and FIG. 8 is a flowchart showing a realtime operation of the ultrasound imaging system according to some embodiments of the present disclosure. The methods shown in FIGS. 7 and 8 are based on the above-mentioned embodiments of the ultrasound imaging system.

In an advance procedure, the CPU 510 page-locks the memory block of a certain size (the first area) in the system memory 530, and sends the address information of that memory block to the front-end unit and the GPU. Further, the CPU 510 page-locks another memory block of a certain size (the second area) in the system memory 530, and sends the address information of that memory block to the GPU (at Step D810). Using these address information enables the front-end unit and the GPU to make a simultaneous access to the first area in the DMA scheme, and enables the GPU to access the second area in the DMA scheme. As described above, the address information may be the physical address of the page-locked area or it may be a virtual address mapped to the physical address.

Then, the transducer array transmits ultrasound signals in response to a drive signal provided by the transmitting unit (S820). At this time, the ultrasound signal to be transmitted may be a beam focused for each scan line, or it may be in a plane wave or divergent wave form.

Next, the transducer array receives a reflected signal of the ultrasound signal transmitted to the object, and converts reflected signal into an electrical signal (i.e., RF signal). The RF signal is digitized and temporarily buffered in the N buffer memories (S830). Before and after the digital conversion, the RF signal may undergo a low-frequency filtering, an anti-aliasing filtering, a pulse compression, a band-pass filtering, an IQ demodulation, decimation and other such processing.

Referring to the physical address of the first area in the system memory, which is transferred from the host PC, the front-end processing circuit sends via the data bus, the channel data buffered in the buffer memory to the destination address in the first area. At this time, a round-robin scheme is applied the outputs of the N buffer memories to generate a data packet. The destination address is assigned so that the data channels are stored for each channel in continuous address spaces (S840).

Next, the CPU can control the GPU to execute at least one sub-process (for example, digital beam forming) of the process for forming an ultrasonic image in a multi-thread processing method (Steps S850 to S870). The GPU accesses the first area of the system memory 530 in the DMA scheme, to copy the channel data stored in the first area to their own local memory (S850). The GPU follows the signal processing pipeline, to perform additional processing, such as a receive beamforming on the channel data (S860). The GPU may perform a DMA transfer of the output (e.g., beamformed data, IQ data after an I/O demodulation and the like) of at least one step in the signal processing pipeline to the second area of the system memory (S870). In particular, when performing the Steps S850 to S870, the GPU uses the concurrent copy and execution scheme.

5. Non-Realtime Operation

Figure 9A:
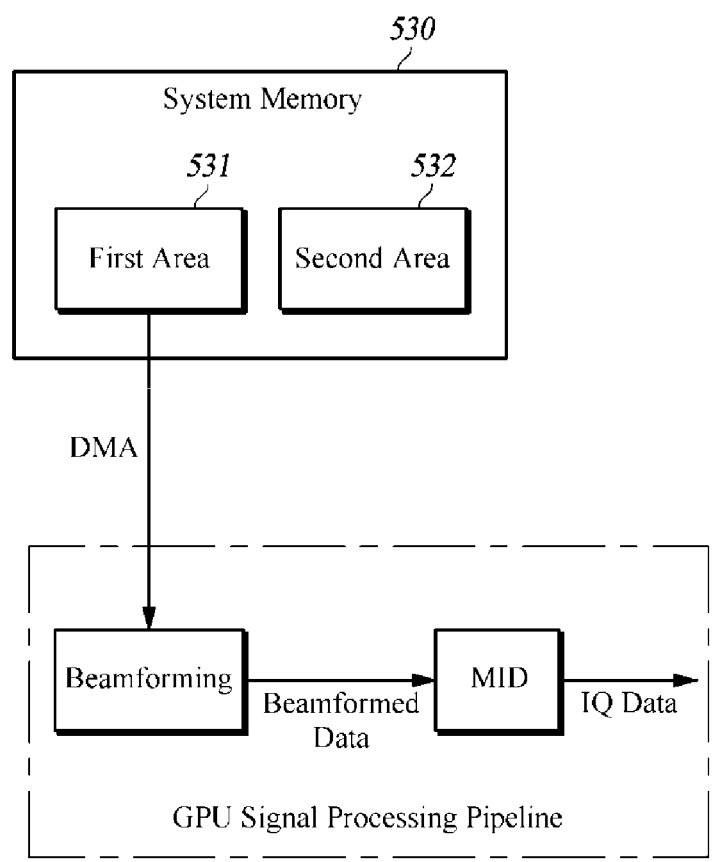
FIGS. 9A and 9B are schematic diagrams showing a method for processing ultrasound data by the host PC when operating in non-realtime according to some embodiments of the present disclosure.
Figure 9B:
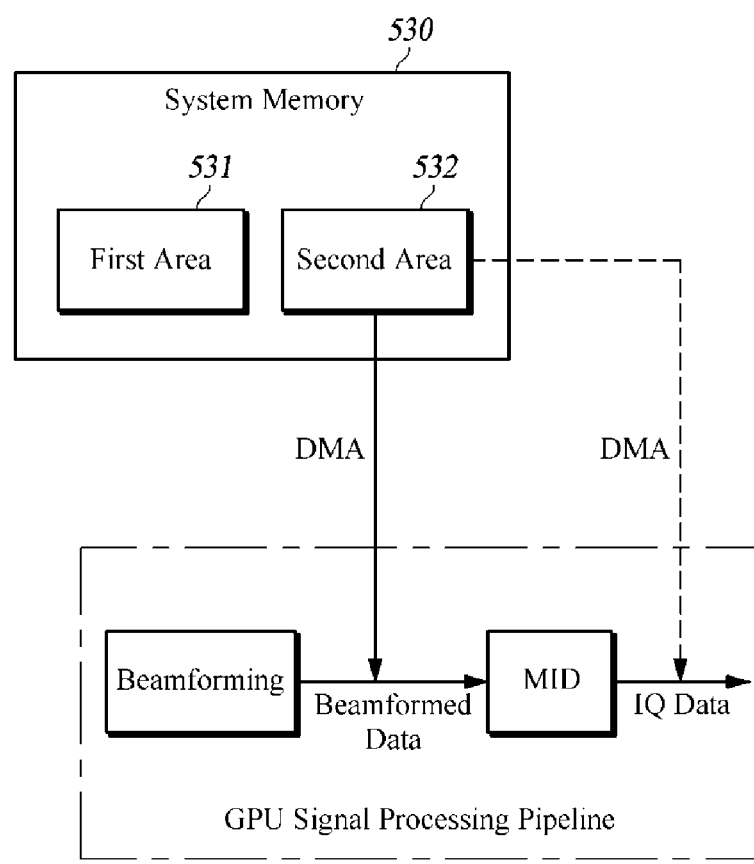
Figure 10A:
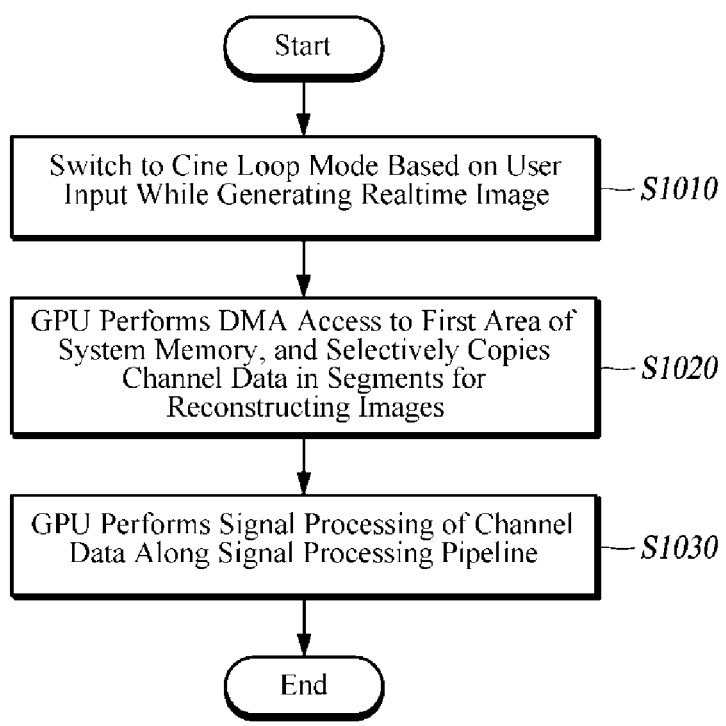
FIGS. 10A and 10B are flowcharts showing methods for processing ultrasound data by the host PC when operating in non-realtime according to some embodiments of the present disclosure.
Figure 10B:
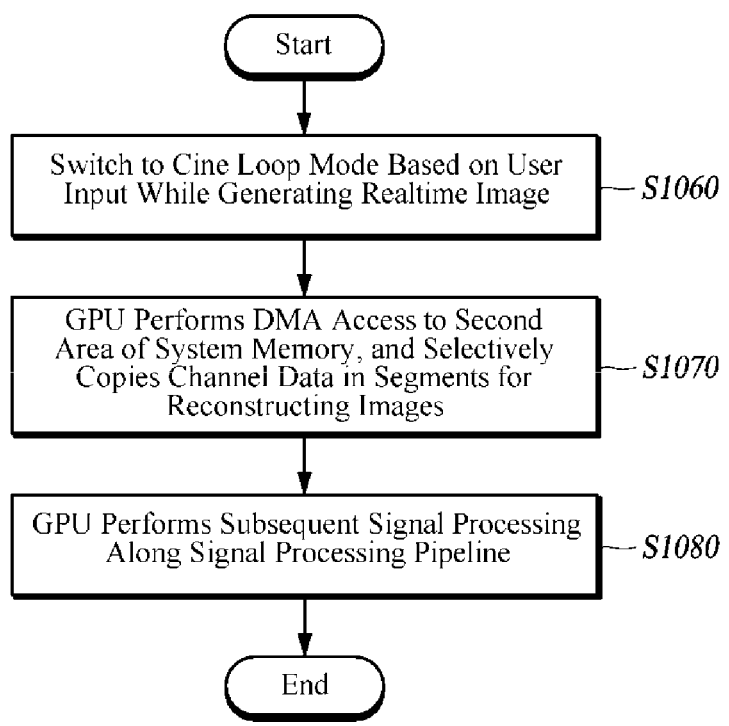

A non-realtime operation of the ultrasound imaging system according to some embodiments of the present disclosure is described in detail below with reference to FIGS. 9A to 10B. FIGS. 9A and 9B are schematic diagrams showing a method for processing ultrasound data by the host PC when operating in non-realtime according to some embodiments of the present disclosure; and FIGS. 10A and 10B are flowcharts showing a method for processing ultrasound data by the host PC when operating in non-realtime according to some embodiments of the present disclosure.

In the course of producing ultrasound images in real time, the ultrasound imaging system is generally responsive to a user input signal for providing a cine loop feature that can playback the ultrasound image containing information about an object, as it was several or a few dozens of seconds back. A typical cineloop memory stores data resulting from a partial processing (e.g., beamforming, IQ demodulation and the like) of the channel data, or data generated data for being displayed. In such a conventional cine loop scheme, the information being played back is destined to be limited by the specific processing method used at the time of storing thereof. This is because the processed data stored in the cine loop memory underwent such operation modes and parameters at the time of their storage that have removed partial information from the channel data.

The ultrasound imaging system according to some embodiments can overcome the limitations of the conventional cine loop scheme by using the system memory of the host PC as a cine loop memory. In other words, in some embodiments, the ultrasound data stored in the first area and/or the second area of the system memory is used as data for cine loop.

An example of using the channel data stored in the first area of the system memory as cine loop data is described with reference to FIGS. 9A and 10A.

During the real-time image generation, the host PC switches to the cine loop operation in response to a particular user input (S1010). In the cine loop operation, the GPU accesses the first area of the system memory 530 in the DMA scheme, and copies the channel data of the sections up for image reconstruction to its own local memories selectively (S1020). In particular, when copying the channel data, rather than the entire frame data of the section to be reconfigured, it is also possible to a selective copy can be made for the scanline data exclusively corresponding to the user-inputted region of interest. The GPU follows the signal processing pipeline, to perform additional processing such as beamforming with respect to the copied channel data (S1030). In particular, the GPU can perform processing by applying different operation modes, processing techniques and the applicable parameters from those applied at the time of entry into the cine loop, and thereby overcome the limitations of the conventional cine loop scheme. Further, some embodiments do not utilize a separate memory but the system memory instead, which is used during real time operation, as a cine loop memory, which is advantageous in that the efficient way of the GPU accessing the system memory as applied during the real time operation is directly inherited to the cine loop operation.

An example of using the data stored in the second area of the system memory as cine loop data is described with reference to FIGS. 9B and 10B. As described above, the data obtained by performing additional processing such as the beamforming and the like on the channel data are stored in the second area.

During the real-time image generation, the host PC switches to the cine loop operation in response to a particular user input (S1060). In the cine loop operation, the GPU makes a DMA-access to the second area of the system memory 530 in which data is stored after an additional process such as beamforming, copies the data of the sections up for image reconstruction to its own local memories selectively (S1070), and performs processing further to those completed on the copied data (S1080). Different from the embodiment of FIGS. 9A and 10A, information to be played back in the present embodiment would be limited by the specific processing method used at the time of storing thereof in the second area of the system memory, but the present embodiment is advantageous in that the efficient way of the GPU accessing the system memory as applied during the real time operation is directly inherited to the cine loop operation.

Although the embodiments illustrates the respective steps as being sequentially performed, they merely instantiate a technical idea of some embodiments. A person having ordinary skill in the pertinent art could appreciate that various modifications, additions, and substitutions are possible by changing the sequences described in the respective embodiments or by executing two or more steps in parallel, without departing from the gist and the nature of the embodiments, and hence the embodiments not limited to the illustrated chronological sequences.

The ultrasound imaging according to some illustrated embodiments can be implemented as computer-readable codes, and can be recorded on a computer-readable recording medium. The computer-readable recording medium on which the codes for implementing the ultrasound imaging are recordable includes any type of recording device on which data that can be read by a computer system are recordable. Examples of the computer-readable recording medium include a magnetic tape, e.g., a ROM, a floppy disk, a hard disk, and the like, an an optically readable medium, e.g., a CD-ROM, DVD, and the like, and also include one implemented in the form of a carrier wave, e.g., transmission through the Internet. Further, the computer-readable recording medium can be distributed in computer systems connected via a network, and computer-readable codes can be stored and executed in a distributed mode.

Although exemplary embodiments of the present disclosure have been described for illustrative purposes, those skilled in the art will appreciate that various modifications, additions and substitutions are possible, without departing from the idea and scope of the claimed invention. Accordingly, one of ordinary skill would understand the scope of the claimed invention is not to be limited by the explicitly described above embodiments but by the claims and equivalents thereof.

REFERENCE NUMERALS

| | |
|---|---|
| 110: Transducer | 120: Front-end unit |
| 130: Host PC | 140: Display unit |
| 210: Transmitting unit | 220: Receiving unit |
| 230: Front-end processing circuit | 510: CPU |
| 520: GPU | 530: System memory |

REFERENCE NUMERALS

| | |
|---|---|
| 531: First area | 532: Second area |
| 540: Bridge chip | 550: Data bus |

The invention claimed is:

1. An ultrasound diagnostic apparatus, comprising:
a front-end unit configured to be electrically connected to a transducer; and
a host PC configured to receive channel data from the front-end unit via a data bus and to process the channel data, wherein
the host PC includes
a system memory,
at least one parallel core processor, and
a central processing unit (CPU) configured to page-lock a predetermined area (hereinafter, "first area") in the system memory;
the front-end unit is configured to transmit the channel data to the first area in a direct memory access (DMA) scheme; and
the parallel core processor is configured to access the first area in the DMA scheme and to perform at least a part of processes for generating an ultrasound image, in a multi-thread processing scheme;
wherein the parallel core processor is configured, when performing at least a part of the processes, to divide the channel data to be stored in the first area into a plurality of blocks and to process divided blocks based on a concurrent copy and execution scheme; and
wherein the channel data is configured to be divided in accordance with a criterion based on an ultrasound transmitting method used when acquiring the channel data.

2. The ultrasound diagnostic apparatus according to claim 1, wherein the front-end unit and the parallel core processor are configured to simultaneously access the first area by using an address information of the first area.

3. The ultrasound diagnostic apparatus according to claim 2, wherein the address information of the first area includes either one of a physical address of the first area and a logical address mapped to the physical address.

4. The ultrasound diagnostic apparatus according to claim 1, wherein the front-end unit is configured to generate a data packet for each channel based on the channel data and to assign a destination address of each data packet such that channel-specific data are stored in continuous address spaces in the first area.

5. The ultrasound diagnostic apparatus according to claim 4, wherein the front-end unit is configured to generate the data packet as large as a maximum payload size of the data bus by applying a round-robin scheme for each channel to the channel data.

6. The ultrasound diagnostic apparatus according to claim 1, wherein each block includes a data set of at least one scanline when the ultrasound transmitting method is to use a focused ultrasound.

7. The ultrasound diagnostic apparatus according to claim 6, wherein a size of the block is determined by at least one of a scan depth, the number of scanlines, an ensemble, a frame rate, or a realtime/non-realtime operation status.

8. The ultrasound diagnostic apparatus according to claim 1, wherein each block includes a data set of a plurality of frames when the ultrasound transmitting method is to use a plane wave.

9. The ultrasound diagnostic apparatus according to claim 8, wherein a size of the block is determined by at least one of a scan depth, the number of scanlines, an ensemble, a frame rate, the number of frames to be compounded, or a realtime/non-realtime operation status.

10. The ultrasound diagnostic apparatus according to claim 1, the ultrasound diagnostic apparatus configured to acquire channel data in an amount exceeding a realtime processing capacity of the host PC.

11. The ultrasound diagnostic apparatus according to claim 10, wherein the parallel core processor is configured to selectively process a part of the channel data to be stored in the first area when the ultrasound diagnostic apparatus operates in realtime.

12. The ultrasound diagnostic apparatus according to claim 10, wherein the parallel core processor is configured to process all the channel data to be stored in the first area or the channel data in at least an amount larger than that processed in a realtime operation when the ultrasound diagnostic apparatus performs a cine loop operation.

13. The ultrasound diagnostic apparatus according to claim 1, wherein the parallel core processor is configured to transmit an output of a predetermined step among the processes for generating the ultrasound image to a second area of the system memory in the DMA scheme.

14. The ultrasound diagnostic apparatus according to claim 13, configured, when performing a cine loop operation, to use at least one of the first area and the second area as a cine memory.

15. The ultrasound diagnostic apparatus according to claim 1, wherein the parallel core processor is configured, when performing at least a part of the processes, to limit usage of an off-chip memory to storage of input data and output data.

16. The ultrasound diagnostic apparatus according to claim 1, wherein the parallel core processor is configured, when performing at least a part of the processes, to use an on-chip memory for storing an interim output.

17. The ultrasound diagnostic apparatus according to claim 1, wherein the parallel core processor comprises any one of a graphics processor unit (GPU), a general-purpose GPU (GPGPU) and a many integrated core (MIC).

18. The ultrasound diagnostic apparatus according to claim 1, wherein the front-end unit comprises a field programmable gate array (FPGA).

19. The ultrasound diagnostic apparatus according to claim 1, wherein the front-end unit comprises a peripheral type device incorporated in the host PC.

20. The ultrasound diagnostic apparatus according to claim 1, wherein the front-end unit comprises a board-to-board (BTB) connection incorporated in a probe.

21. A host PC for an ultrasound diagnostic apparatus that includes a front-end unit configured to be electrically connected to a transducer and a host PC configured to receive channel data from the front-end unit via a data bus and to process the channel data, the host PC comprising:
   a system memory;
   at least one parallel core processor; and
   a central processing unit (CPU) configured to page-lock a predetermined area (hereinafter, "first area") in the system memory, wherein
   the front-end unit is configured to perform a transmission of the channel data to the first area in a direct memory access (DMA) scheme, and
   the parallel core processor is configured to access the first area in the DMA scheme and to perform at least a part of processes for generating an ultrasound image, in a multi-thread processing scheme;
   wherein the parallel core processor is configured, when performing at least a part of the processes, to divide the channel data to be stored in the first area into a plurality of blocks and to process divided blocks based on a concurrent copy and execution scheme; and
   wherein the channel data is configured to be divided in accordance with a criterion based on an ultrasound transmitting method used when acquiring the channel data.

22. The host PC according to claim 21, wherein the channel data are stored simultaneously with the transmission by the front-end unit in continuous address spaces in the first area for each channel.

23. The host PC according to claim 21, wherein each block includes a data set of at least one scanline when the ultrasound transmitting method is to use a focused ultrasound.

24. The host PC according to claim 21, wherein each block includes a data set of a plurality of frames when the ultrasound transmitting method is to use a plane wave.

25. The host PC according to claim 21, wherein the parallel core processor is configured to selectively process a part of the channel data to be stored in the first area when the ultrasound diagnostic apparatus operates in realtime.

26. The host PC according to claim 21, wherein the parallel core processor is configured to transmit an output of a predetermined step among the processes for generating the ultrasound image to a second area of the system memory in the DMA scheme.

27. The host PC according to claim 26, wherein the ultrasound diagnostic apparatus is configured, when performing a cine loop operation, to use at least one of the first area or the second area as a cine memory.

28. A method for generating an ultrasound image by an ultrasound diagnostic apparatus that includes a front-end unit configured to be electrically connected to a transducer and a host PC configured to receive channel data from the front-end unit via a data bus and to process the channel data, the method comprising:
   page-locking, by the host PC, a predetermined area (hereinafter, "first area") in a system memory;
   acquiring, by the front-end unit, the channel data by using the transducer;
   transmitting, by the front-end unit, the channel data to the first area; and
   performing processes for generating an ultrasound image based on the channel data by using a central processing unit (CPU) and a parallel core processor included in the host PC, wherein
   the front-end unit and the parallel core processor are configured to simultaneously access the first area in a direct memory access (DMA) scheme;
   the parallel core processor is configured, when performing at least a part of the processes, to divide the channel data to be stored in the first area into a plurality of blocks and to process divided blocks based on a concurrent copy and execution scheme; and
   the channel data is configured to be divided in accordance with a criterion based on an ultrasound transmitting method used when acquiring the channel data.

29. The method according to claim 28, wherein the parallel core processor is configured to perform at least a part of the processes for generating the ultrasound image, in a multi-thread processing scheme.

30. The method according to claim 28, wherein the front-end unit is configured to generate a data packet of the channel data for each channel based on the channel data and to assign a destination address of each data packet such that channel-specific data are stored in continuous address spaces in the first area.

31. The method according to claim 28, wherein each block includes a data set of at least one scanline when the ultrasound transmitting method is to use a focused ultrasound.

32. The method according to claim 28, wherein each block includes a data set of a plurality of frames when the ultrasound transmitting method is to use a plane wave.

33. The method according to claim 28, wherein the parallel core processor is configured to selectively process a part of the channel data to be stored in the first area when the ultrasound diagnostic apparatus operates in realtime.

34. The method according to claim 28, wherein the parallel core processor is configured to transmit an output of a predetermined step among the processes for generating the ultrasound image to a second area of the system memory in the DMA scheme.

35. The method according to claim 34, wherein the ultrasound diagnostic apparatus, when performing a cine loop operation, is configured to use at least one of the first area and the second area as a cine memory.

* * * * *